United States Patent [19]
Delmore et al.

[11] Patent Number: 5,997,492
[45] Date of Patent: Dec. 7, 1999

[54] ORTHOPEDIC CASTING ARTICLES CONTAINING BACKINGS HAVING WATER SOLUBLE BINDERS

[75] Inventors: Michael D. Delmore, Moundsview; Paul E. Hansen, Lake Elmo, both of Minn.

[73] Assignee: 3M Innovative Properties Company, St. Paul, Minn.

[21] Appl. No.: 08/994,601

[22] Filed: Dec. 19, 1997

[51] Int. Cl.$^6$ .......................................................... A61F 5/00
[52] U.S. Cl. ........................................ 602/8; 602/5; 602/6
[58] Field of Search ................................. 602/8, 6, 13, 5

[56] References Cited

U.S. PATENT DOCUMENTS

| | | | |
|---|---|---|---|
| 3,908,644 | 9/1975 | Neinart et al. ............................. | 128/90 |
| 4,131,114 | 12/1978 | Kirkpatrick et al. ...................... | 128/90 |
| 4,411,262 | 10/1983 | Von Bonin et al. ....................... | 128/90 |
| 4,473,671 | 9/1984 | Green ...................................... | 523/105 |
| 4,502,479 | 3/1985 | Garwood et al. ......................... | 128/90 |
| 4,667,661 | 5/1987 | Scholz et al. ............................. | 128/90 |
| 4,668,563 | 5/1987 | Buese et al. .............................. | 428/230 |
| 4,841,958 | 6/1989 | Ersfeld et al. ............................. | 128/90 |
| 4,856,502 | 8/1989 | Ersfeld et al. ............................. | 128/90 |
| 5,342,291 | 8/1994 | Scholz et al. ............................. | 601/41 |
| 5,346,939 | 9/1994 | Moren et al. ............................. | 524/176 |
| 5,405,643 | 4/1995 | Scholz ..................................... | 427/2.31 |
| 5,423,735 | 6/1995 | Callinan et al. ............................ | 602/8 |
| 5,449,550 | 9/1995 | Yasis et al. ............................... | 428/254 |
| 5,498,232 | 3/1996 | Scholz ..................................... | 602/8 |
| 5,505,692 | 4/1996 | Cho .......................................... | 602/8 |
| 5,540,652 | 7/1996 | Callinan et al. ............................ | 602/1 |
| 5,607,387 | 3/1997 | Martin et al. ............................. | 602/8 |

FOREIGN PATENT DOCUMENTS 1 491 190   3/1969   Germany.

*Primary Examiner*—John G. Weiss
*Assistant Examiner*—Kelvin E. Hart
*Attorney, Agent, or Firm*—Eloise J. Maki

[57] ABSTRACT

An orthopedic casting article containing a fibrous backing stabilized with a water soluble binder and having a hardenable material applied thereto is described. Methods of making and using such orthopedic casting articles are also described.

23 Claims, No Drawings

ORTHOPEDIC CASTING ARTICLES CONTAINING BACKINGS HAVING WATER SOLUBLE BINDERS

FIELD

This invention relates to materials useful in orthopedic casting, and more particularly to orthopedic casting articles, such as tapes and splints, containing fibrous backings stabilized with water soluble binders, wherein the fibrous backing contains a hardenable material.

BACKGROUND OF THE INVENTION

A variety of orthopedic casting materials useful in the immobilization of broken or injured limbs are known in the art. Among the first materials developed for this purpose were plaster of Paris bandages, which provided good moldability and palpability of fine bone structure, but which suffered from a number of disadvantages, including a low strength-to-weight ratio and slow strength build-up. Casting materials were later developed that addressed the problems associated with plaster of Paris bandages. For example, knitted fiberglass fabrics coated with water curable polyisocyanate prepolymer resins were developed which provided higher strength-to-weight ratios and improved air permeability. These materials, however, are not as compressible as plaster, tend to mask fine bone structure as the cast is applied, and are expensive to make.

Efforts continue in the art to provide orthopedic casting materials having good moldability, good palpability of fine bone structure, good extensibility, and fast strength build-up during application, and also having good strength-to-weight ratios and good air permeability after curing.

SUMMARY OF THE INVENTION

The present invention relates to articles having a fibrous backing containing a water soluble binder. The binder-containing fibrous backing further contains a hardenable material to provide an article, preferably usable in a water-hardenable medical dressing capable of immobilizing and/or supporting a body part, i.e., as an orthopedic casting article. This combination of materials provides a casting material that is dimensionally stable prior to wetting. The invention is particularly useful for providing orthopedic casting articles containing non-woven fibrous backings, as well as for casting articles containing microcreped or compacted fibrous backings. Upon wetting, the stiffness of the backing drops dramatically (approaching negligible stiffness in certain embodiments) due to penetration of water into the backing and solubilization of the binder. After sufficient wetting time to solubilize the binder, the resultant wetted article may be used as an orthopedic casting article, such as a tape or splint. If a non-woven fibrous backing is employed, the wetted article is held together by the viscosity of the hardenable material, the presence of any residual binder, and any slight entanglements or other physical interactions between the fibers of the fibrous backing. The article is then highly moldable and, in preferred embodiments, may be torn with ease. If a microcreped or compacted fibrous backing is used, the water soluble binder stabilizes the backing by retaining very low strength stretch that is typically lost in resin coating, slitting, and winding processes, and preserving desirable elongation properties for end use.

Fibrous materials for use in the fibrous backing of the present invention include those that may be dimensionally stabilized with a water soluble binder, that upon wetting become highly moldable, and that may be combined with a hardenable resin to provide orthopedic casting articles. The fibrous backing may comprise a blend of staple crimped fibers and straight fibers. In preferred embodiments of the invention, the fibrous backing comprises a carded non-woven web. The fibrous backing may also comprise a microcreped or compacted woven, non-woven, or knit fabric. In other embodiments, the fibrous backing may further include a particulate or fibrous filler. Non-woven fibrous webs are a preferred class of materials for use in the fibrous backing, and carded non-woven fibrous materials are especially preferred. The non-woven fibrous backings may comprise straight or crimped fibers, and combinations thereof.

Suitable water soluble binders for use in the present invention include binders that are compatible with the fibrous backing material and that impart dimensional stability to the backing. A preferred water soluble binder is polyvinylpyrrolidone.

The orthopedic casting articles of this invention are preferably dimensionally stable before exposure to water. Upon exposure to water, the articles become initially moldable, pliable, and conformable as the water soluble binder dissolves. In addition the articles are preferably tearable after wetting.

The orthopedic casting articles of the invention contain a hardenable material. The hardenable material may be in the form of a coating on the fibrous backing, may be impregnated in the fibrous backing, or associated with the fibrous backing in accordance with any method shown in the art. The hardenable material preferably is water hardenable, and may include materials such as plaster of Paris or hardenable resins.

Where the hardenable material includes a hardenable resin, the resin preferably is a water curable resin. Particularly preferred water curable resins are the isocyanate-functional prepolymers. The water curable resin may also be selected from the group including the liquid organometallic compounds, alkoxy silane functional polyurethane oligomers, hardenable silicate-containing compositions and epoxy resins.

In another aspect, the invention features a method of making an orthopedic casting article. The method involves applying a hardenable resin to a fibrous backing that contains a water soluble binder.

In still another aspect, the invention features a method of immobilizing a limb. The method involves the steps of: wetting an orthopedic casting article that comprises a fibrous backing containing a water soluble binder, the fibrous backing further containing a hardenable material; and applying the orthopedic casting article to the limb such that the limb is immobilized upon hardening of the hardenable material.

As described herein, the present invention has several advantages. The orthopedic casting articles of this invention are dimensionally stable before use, and transform into highly moldable, and preferably tearable, materials upon wetting and application. Among other advantages, the articles provide good palpability of fine bone structure and good extensibility and dead-stretch properties during application, and have good strength-to-weight ratios and air permeability after cure. The ability to easily tear the article after wetting, in certain preferred embodiments, provides a distinct advantage over presently available orthopedic casting materials. The ability to retain very low strength stretch in embodiments of the invention containing compacted or microcreped fibrous backings stabilized with a water soluble binder also provides a distinct advantage over presently available orthopedic casting materials.

Other advantages of the invention will be apparent from the following description and the appended claims.

DETAILED DESCRIPTION OF THE INVENTION

In general, the present invention features articles in which a fibrous backing contains a water soluble binder and a hardenable material associated with the fibrous backing. Preferably, the articles are usable as orthopedic casting articles.

The fibrous backing of the orthopedic casting articles of the present invention may be prepared using a variety of materials and methods. In general, suitable fibrous materials for use in the present invention include those that (1) may be dimensionally stabilized with a water soluble binder, (2) upon wetting become highly moldable and (3) may be combined with a hardenable material to provide an orthopedic casting article having high moldability during application and desirable strength-to-weight ratios upon cure.

One preferred class of fibrous backings suitable for use in the present invention are the "non-wovens." There are many known types of non-woven materials suitable for use in this invention, and many known processes for preparing such materials. For example, an air laid process commonly known as a "Rando Webber," and a wet laid process such as a paper process, are suitable. These and other known processes create non-woven webs with substantially less fiber orientation than a "carded" non-woven web.

Carded non-woven webs represent an especially preferred class of fibrous backings for use in the orthopedic casting materials of the present invention. Carded non-woven webs and processes for making them are well-known in the art. In a typical carding process, a carded web line starts with a fiber opening process, followed by a carding process. In the carding process, random loose fibers enter one end of the process, and at the other end a uniform but relatively weak non-woven web emerges. At this point, the carded non-woven web has little or no tensile strength, and must be treated with an additional process or processes that impart tensile strength to the carded web. Such processes known in the art include roll coating, needle-punching, stitch bonding, and thermal calendering. In preferred embodiments of this invention, a carded non-woven web is coated with a water soluble binder to stabilize the carded web and impart tensile strength to it.

Carded non-woven fibrous backings are preferred for use in the orthopedic casting materials of the present invention. The carding process, as described above, produces webs with a high degree of fiber orientation in the machine direction, compared with non-woven webs prepared by other processes. It is believed that the fiber orientation produced by the carding process is advantageous in terms of handling and final cured product strengths when used in an orthopedic casting material of this invention. For example, a high degree of fiber orientation maximizes the extensibility of the non-woven prior to breaking it in the machine direction.

Suitable fibers for use in non-woven fibrous backings include straight and crimped fibers of polyester, rayon, cotton, nylon, acrylic, polyethylene, polypropylene, fiberglass, polyacrylamide, carbon, and combinations or blends thereof For example, a carded non-woven fibrous backing can be made from a staple crimped fiber such as rayon, polyester, fiberglass, polyolefins such as polypropylene, nylon, aramids such as Kevlar and Nomex (both available from Dupont), carbon, graphite, polybenzimidazole, and blends thereof. Additional straight fibers may also be incorporated in non-woven fibrous backings. Suitable straight fibers include high tenacity polyester cord, polyolefins such as Allied Spectra fiber, ceramic fibers, fiberglass, aramid, carbon and graphite fiber.

It is desirable to provide orthopedic casting articles having good extensibility. With respect to non-woven fibrous backings, extensibility can be enhanced by incorporating different types of fibers and fibers of different lengths. In general, a non-woven fibrous backing containing short fibers has a low percent elongation at break, and non-woven backings containing long fibers have higher percent elongation at break. Fiber composition also plays a role in extensibility properties. For example, in the presence of water, cotton and rayon fibers exhibit greater extensibility compared with polyester fibers of equal length, because the cotton and rayon fibers are hydrophilic and exhibit a higher degree of cohesiveness, tending to cling together to increase the degree of elongation.

Additional suitable fibrous backing materials include compacted or microcreped fabrics. These materials are described in U.S. Pat. Nos. 5,405,643; 5,498,232; 5,505,692; 4,668,563; and 5,449,550, which are herein incorporated by reference. Microcreped and compacted fabrics exhibit a high degree of elongation. Such fabrics may include microcreped or compacted non-woven, woven, or knit fabrics.

The fibrous backing in the orthopedic casting materials of the present invention contains a water soluble binder. Suitable water soluble binders include any water soluble polymer and/or copolymer that is compatible with the fibrous backing material and that imparts desired dimensional stability to the backing. Many water soluble polymers and/or copolymers are known. Nonlimiting examples of such polymers and copolymers suitable for use as binders include polyvinylpyrrolidones, polyvinylpyrrolidone/vinyl acetate copolymers, polyvinyl alcohols, carboxymethyl celluloses, hydroxypropyl cellulose starches, polyethylene oxides, polyacrylamides, polyacrylic acids, cellulose ether polymers, polyethyl oxazolines, esters of polyethylene oxide, esters of polyethylene oxide and polypropylene oxide copolymers, urethanes of polyethylene oxide, and urethanes of polyethylene oxide and polypropylene oxide copolymers. A preferred water soluble binder for use in the fibrous backings of the present invention is polyvinylpyrrolidone (PVP). For example, in one preferred embodiment of the invention a carded non-woven fibrous backing contains a 90,000 molecular weight PVP.

The water soluble binder helps impart dimensional stability to the fibrous backing. In embodiments of the invention in which a non-woven fibrous backing is employed, the binder helps to hold the non-woven fibers together, transforming a loose web of fibers into a stable, "felt-like" fabric. Among other advantages, the stability imparted by the water soluble binder to the non-woven web allows the non-woven to be coated or impregnated with a curable resin. If desired, the water soluble binder may be applied to a non-woven web as a processing step in the preparation of the web, for example just aster a carding process to form a carded non-woven web stabilized with a water-soluble binder. Preferably, the non-woven web is saturated with the water soluble binder (e.g. the water soluble binder in a solution containing the binder and deionized water), followed by drying. Upon wetting, the binder solubilizes, and the article loses much, and in some embodiments nearly all, of its stiffness, developing a consistency resembling that of wet tissue paper (where a non-woven fibrous backing is employed). This consistency makes the article very easy to manipulate in applying the article to immobilize a limb.

In embodiments of the invention in which a compacted or microcreped non-woven, knit, or woven fibrous backing is employed, the addition of a water soluble binder stabilizes the backing. Microcreped and compacted fabrics exhibit exceptional elongation properties, however much of the elongation gained by the microcreping or compacting may be lost because it can be pulled out with a very low amount of force, as might be imparted during fabric coating, winding, or slitting. Advantageously, a water soluble binder can be employed to stabilize the fabric, allowing it to withstand the tensions applied in these processes. During use, the binder solubilizes upon wetting, and the retained extensibility is available to the end user, not having been lost in the process of manufacturing the article. The water soluble binder may be applied to compacted or microcreped fibrous backings by any of various coating methods, such as spraying, roll coating, foaming, curtain and dip coating. Preferably, the fabric is saturated with the water soluble binder, followed by drying.

Additional particulate and/or non-cardable fibrous fillers can be added to the casting article. Examples of such particulate fillers are carbon black, talc, calcium carbonate, silica, mica, hollow microspheres such as glass bubbles, solid microspheres like fly ash or glass spheres, diatomaceous earth and the like. Examples of non-cardable fibrous materials include wallastonites, short fiber length chopped glass or carbon fiber, fibrous pulps such as cellulose and synthetic pulps such as polyolefins and aramids, metal fibers made from various elements or blends thereof and whiskers. If desired, these types of materials can be added to the non-woven, using standard methods known in the art, to improve, for example, the resin holding capacity of a given resin or to improve the final composite compression strengths of the article.

In the orthopedic casting materials of the present invention, the fibrous backing containing the water soluble binder further contains a hardenable material. Suitable hardenable materials useful in this invention include materials that can be applied to a fibrous backing and which can then be cured to reinforce the fibrous backing. Such materials may include plaster of Paris or any of a variety of curable resins known in the art.

If a resin is employed the resin is preferably curable to a crosslinked thermoset state. The preferred curable resins are fluids, i.e., compositions having viscosities between about 5 Pa s and about 500 Pa s, more preferably between about 10 Pa s to about 100 Pa s.

The hardenable material used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin preferably is sufficiently reactive with the curing agent to insure rapid hardening of the cast once it is applied but not so reactive that it does not allow sufficient working time to apply and shape the cast. Initially, the casting material is pliable and formable and in the case of casting tapes should adhere to itself Then, in a short time following completion of application, it should become rigid or, at least, semi-rigid, and strong to support loads and stresses to which the article is subjected by the activities of the wearer. Thus, the material must undergo a change of state from a fluid-like condition to a solid condition in a matter of minutes.

The preferred resins are those cured with water. Presently preferred are urethane resins prepared by the reaction of a polyisocyanate and a polyoyl such as those disclosed in U.S. Pat. No. 4,131,114, which is herein incorporated by reference. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. The solutions may also contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system).

Some presently more preferred resins for use in the present invention are water-curable, isocyanate-functional prepolymers. Suitable systems of this type are disclosed, for example, in U.S. Pat. Nos. 4,411,262 and 4,502,479, which are herein incorporated by reference. An example of a preferred resin system of this type is disclosed in U.S. Pat. No. 4,667,661, which is herein incorporated by reference. A "water-curable isocyanate-functional prepolymer," as that term is used herein, refers to a prepolymer derived from a polyisocyanate, preferably aromatic, and a reactive hydrogen compound or oligomer. The prepolymer has sufficient isocyanate functionality to cure upon exposure to water, e.g. moisture vapor, or preferably liquid water.

The above-described hardenable resins, and methods of applying (e.g., coating) them onto fabrics, are described, for example, in U.S. Pat. No. 5,449,550. Other classes of preferred water-curable resins are non-isocyanate resins such as water reactive liquid organometallic compounds (as described in U.S. Pat. No. 5,346,939, which is herein incorporated by reference) and alkoxysilane terminated resins (as described in U.S. Pat. Nos. 5,540,652 and 5,423,735, which are herein incorporated by reference). Yet another preferred non-isocyanate resin system for use in orthopedic casting materials are hardenable silicate-containing compositions as described in Attorney Docket No. 53089USA5A, filed on Nov. 11, 1997, which is herein incorporated by reference.

The orthopedic casting articles of the present invention may also include effective amounts of various additives such as fillers, polymeric toughening agents, drying agents, binding agents, hydrophobic materials, antifoaming agents, lubricants, slip agents, stabilizers, tackifiers, pigments, dyes, and fragrances. One or more of these additives may be incorporated into the articles of the present invention. They are each used in "an effective amount," i.e., an amount sufficient to provide one or more of the benefits of such an additive. Examples of lubricants which may be used in the present invention include bound lubricants and additive lubricants, which are described in U.S. Pat. No. 4,856,502, which is incorporated herein by reference.

The orthopedic casting articles of the present invention may be fabricated in the form of a tape, or as rolls of such tape, in accordance with methods well known in the art. The casting articles may also be fabricated in the form of a splint. For example, multiple layers of the casting article may be layered together (with the hardenable resin coating preferably providing adhesion between layers), and used as a splint material. The orthopedic casting articles may be packaged in similar fashion to other resin coated orthopedic casting materials.

The invention features, in another aspect, a method of making an orthopedic casting article. The method includes the step of applying a hardenable material to a fibrous backing, wherein the fibrous backing contains, and is stabilized with, a water soluble binder, as described herein.

In use, for example in the immobilization of a limb, an orthopedic casting article of this invention can be removed from any packaging material and (if a water-hardenable material is coated on the fibrous backing) contacted with water (e.g. by submersion). After sufficient wetting time, the article (e.g. a roll of tape) can be removed from the water and squeezed. The tape can be unrolled and applied to a limb. In preferred embodiments of the invention, e.g. where a carded non-woven fibrous backing is employed, the wetted article is highly moldable and extensible, and exhibits the highly advantageous characteristic of being easily tearable. This feature makes the orthopedic casting article much easier to use, compared with currently available casting materials that are not easily tearable, and allows the user to tear portions of the wetted article and apply them to areas where additional support is needed.

The invention features, in still another aspect, a method of immobilizing a limb. The method includes the steps of: wetting an orthopedic casting article that includes a fibrous backing containing a water soluble binder, the fibrous backing further containing a hardenable material; and applying the orthopedic casting article to the limb such that the limb is immobilized upon hardening of the hardenable material.

The invention may be illustrated by way of the following examples.

EXAMPLES

Example 1

Carded Non-woven Fabric Backings Containing Water Soluble Binder

A random double doffer card (Model WZM/K5-d2-R2, Hergeth Hollingsworth, Dulmen, Germany) was employed to convert different types of fiber materials into various fibrous fabric backings of non-woven construction.

The fibers were batch weighed and hand blended before being placed into a fiber opening unit which preceded the Hergeth card. The resulting backings consisted of a uniform mat of loose fibers with a high degree of machine direction orientation and little or no dimensional stability or tensile strength. Fiber materials of different composition, structure, denier, fiber length, and basis weight were utilized and are listed in Table 1A. The Minifiber straight high tenacity (HT) polyester (PET) fibers were additionally passed through a Cadette 500 Fiber Opener (Laroche Co., France) before being added to the fiber opening unit.

Immediately following the carding process, the non-woven fabric backings were coated with an aqueous binder solution utilizing a two-roll gravure type pad coating station. The binder solution contained either 10% polyvinylpyrrolidone (PVP K-30, 30,000 MW, BASF, Wyandotte, Mich.) or 6% polyvinylpyrrolidone (PVP K-90, 90,000 MW, BASF, Wyandotte, Mich.) in deionized water. The pad coating station consisted of a spiral grooved silicone upper roll and a typical gravure bottom roll. To thoroughly coat and saturate the non-woven fabric backings, the binder solution was first processed through a Custom Foamer (Less Inc., Dalton, Ga.), which whipped nitrogen gas into the binder solution. A surfactant, 0.5% TRITON™ GR-5 (Union Carbide, Danbury, Conn.), was added to help stabilize the foam, which had the consistency of shaving cream. The foamed binder solution was then pumped to the top roll of the pad coating station and distributed across the top of the roll through a coat hanger style die.

After passing through the pad coating station, the binder-containing non-woven fabric backings were dried in a standard two-zone air flow oven (Industrial Heat Enterprises) equipped with an open mesh belt which supported the backings through the oven. The oven was operated at temperatures between about 85° C. and 162° C. Upon exiting the oven, the backings were rolled-up by using a conventional single spindle winding station.

The basis weights and the tensile strengths (according to ASTM Test Method No. D3759-83) of the dried non-woven fabric backings containing PVP binder were measured and the results are provided in Tables 1A and 1B, respectively. The backing samples were then re-wetted using the procedure described below and tensile strengths of the wet samples were determined using the same ASTM Test Method. Results are provided in Table 1C.

Re-wetting Procedure: A 10.7-cm×15.2-cm sponge was placed in the bottom of a tray filled with distilled water and squeezed several times until completely wetted. The sponge was turned over and a 7.6 cm×15.2 cm sample of backing was immediately placed across the sponge width, thereby contacting 10.7 cm of the sponge with the sample. The sample was then patted down onto the sponge by hand and allowed to stay in contact with the sponge for 15 seconds or until the sample was saturated with water. The sample was then carefuully lifted from the sponge, placed in the clapping jaws of an Instron Tensile Strength Tester, and tested according to the ASTM Method.

TABLE 1A

Carded Non-woven Fabric Backings Containing PVP Binder

| Run | Fiber Input Material | Fiber Basis Weight (g/m$^2$) | Added Binder | Added Binder Basis Weight (g/m$^2$) |
|---|---|---|---|---|
| 1A | 100% Courtaulds Rayon Type 10668 (1.5 dpf × 3.8 cm) (Courtaulds Fibers Inc., New York, NY) | 20.0 | PVP K-90 | 6.0 |
| 1B | 100% Lenzing Rayon (1.5 dpf × 3.8 cm) (Lenzing Fiber Corp., Charlotte, NC) | 23.0 | PVP K-30 | 4.8 |
| 1C | 80% Minifiber Straight HT PET (3 dpf × 6.3 cm) (MiniFiber Inc., Johnson City, TN) 20% T-121 PET (1.2 dpf × 3.8 cm) (Hoechst Celanese, Charlotte, NC) | 34.0 | PVP K-30 | 5.6 |
| 1D | 80% T-121 PET (1.2 dpf × 3.8 cm) 20% Black Crimped PET (3 dpf × 7.6 cm) (Martin ColorFi, Edgefield, SC) | 74.0 | PVP K-90 | 36.9 |
| 1E | Same as 1D, except non-woven fiber material was thermal calendered at about 135° C. and a force of about 36 kg per linear mm | 74.0 | PVP K-90 | 36.9 |

TABLE 1B

Dry Tensile Strengths

| Run | Elongation at Break (%) | Force at Break (gf/cm width) | Force at X % Elongation (gf/cm width) 2% | 4% | 6% |
|---|---|---|---|---|---|
| 1A | 6.7 | 97.3 | 68.9 | 96.9 | 95.1 |
| 1B | 3.0 | 56.0 | 53.5 | 51.8 | 32.5 |
| 1C | 1.5 | 40.7 | 31.7 | 31.7 | 12.3 |
| 1D | 6.2 | 124.4 | 108.9 | 120.7 | 122.8 |
| 1E | 11.9 | 181.6 | 119.5 | 141.1 | 154.1 |

TABLE 1C

Wet Tensile Strengths

| Run | Elongation at Break (%) | Force at Break (gf/cm width) | Force at X % Elongation (gf/cm width) 2% | 4% | 6% |
|---|---|---|---|---|---|
| 1A | 49.1 | 1.8 | 0.2 | 0.3 | 0.3 |
| 1B | 20.6 | 1.2 | 0.4 | 0.6 | 0.7 |
| 1C | 6.8 | 1.2 | 0.8 | 0.8 | 0.8 |
| 1D | 34.0 | 3.5 | 0.9 | 1.4 | 1.5 |
| 1E | 10.1 | 2.4 | 1.4 | 1.9 | 2.2 |

As shown by the results in Table 1B, the addition of PVP binder to the loosely matted non-woven fabric backings provided materials with sufficient dry tensile strength (force at break greater than about 40 gf/cm width) for subsequent processing, such as would occur with the winding and unwinding of backing rolls during resin coating. In contrast, all of the backings containing binder had very low wet tensile strengths (Table 1C), a result which is attributable to the solubilization of the PVP binder upon saturation of the backing with water. These latter values would approach the inherent tensile strengths of the wet non-woven fabric backings without binder.

Example 2

Microcreped Non-woven and Knit Fabric Backings Containing Water Soluble Binder

A roll of SONTARA™ 8043 (hydroentangled polyester non-woven, DuPont, Wilmington, Del.) was microcreped according to the procedure described in U.S. Pat. No. 5,498,232, the disclosure of which is incorporated herein by reference. A roll of MICROMATIQUE Polyester (available from DuPont and texturized by Unifi Inc., Greensboro, N.C.) was knit and microcreped according to the procedure described in the same patent (U.S. Pat. No. 5,498,232). Samples of both the non-woven SONTARA™ polyester (10.2 cm×1.8 m) and knit polyester (9.2 cm×1.8 m) microcreped fabric backings were carefully placed onto silicone-coated paper. The basis weights of the backing materials are listed in Table 2A. A binder solution containing 10% PVP K-30 in deionized water was hand sprayed over the top of some of the backing samples, which were then dried in a 60° C. oven for approximately two hours. The remaining backing samples were not sprayed with binder solution. The basis weights and the tensile strengths (according to ASTM Test Method No. D3759-83) of the dried samples with and without PVP binder were measured as described in Example 1 and the results are provided in Tables 2A and 2B, respectively. The backing samples were then re-wetted using the procedure described in Example 1 and tensile strengths of the wet samples were determined using the same ASTM Test Method. Results are provided in Table 2C.

TABLE 2A

Microcreped Non-woven and Knit Fabric Backings With and Without PVP Binder

| Run | Starting Backing Material | Fiber Basis Weight (g/m²) | Added PVP Binder | Added Binder Basis Weight (g/m²) |
|---|---|---|---|---|
| 2A | Microcreped SONTARA ™ 8043 | 107 | None | 0 |
| 2B | Microcreped SONTARA ™ 8043 | 107 | K-30 | 24.2 |
| 2C | Microcreped Polyester Knit | 172 | None | 0 |
| 2D | Microcreped Polyester Knit | 172 | K-30 | 44.0 |

TABLE 2B

Dry Tensile Strengths

| Run | Elongation at Break (%) | Force at Break (gf/cm width) | Force at X % Elongation (gf/cm width) | | |
|---|---|---|---|---|---|
| | | | 2% | 4% | 6% |
| 2A | 83.0 | 4214 | 8.8 | 17.2 | 26.9 |
| 2B | 63.0 | 4809 | 89.9 | 172.3 | 238.9 |
| 2C | 89.2 | 4754 | 3.6 | 7.1 | 8.9 |
| 2D | 91.0 | 4954 | 12.0 | 18.2 | 24.9 |

TABLE 2C

Wet Tensile Strengths

| Run | Elongation at Break (%) | Force at Break (gf/cm width) | Force at X % Elongation (gf/cm width) | | |
|---|---|---|---|---|---|
| | | | 2% | 4% | 6% |
| 2A | 74.5 | 3337 | 10.1 | 16.7 | 25.6 |
| 2B | 68.7 | 2944 | 9.3 | 18.5 | 28.7 |
| 2C | 92.5 | 4900 | 2.7 | 5.3 | 8.5 |
| 2D | 88.1 | 4754 | 4.9 | 6.7 | 8.0 |

As shown by the results in Tables 2B and 2C, all of the microcreped non-woven and knit fabric backing samples (with and without PVP binder) provided materials with high dry tensile strengths (force at break greater than about 4200 gf/cm width) and high wet tensile strengths (force at break greater than about 2900 gf/cm width).In addition, based on the dry tensile strength results, the addition of PVP binder, but was increased to 172.3 gf/cm with PVP binder. Therefore, in subsequent processing, such as would occur with the winding and unwinding of backing rolls during resin coating, it is expected that much less stretch would be lost in fabric backings with binder then would be lost in backings with no binder present.

Example 3

Fabric Backings with Binder and Hardenable Resin (Orthopedic Casting Tapes and Articles)

The purpose of this example was to coat sample fabric backings from Example 1 with a hardenable resin and evaluate the resulting orthopedic casting tapes articles for ease of use and for potential cast and splint applications. A liquid isocyanate-terminated polyurethane prepolymer water-curable resin was prepared by combining the ingredients listed in Table 3 according to the following procedure. The ingredients of the Isocyanate Component (Part A) and the ingredients of the Polyol Component (Part B) were mixed under nitrogen in separate glass vessels and stored in sealed glass jars. The jar containing Component B was placed in an oven at 65° C. for at least 14 hours prior to use. Just prior to coating, the jars containing Parts A and B were shaken and the components combined into a third jar which was also shaken. The combined and well-mixed components were then immediately transferred to the coating apparatus.

TABLE 3

Polyurethane Prepolymer Resin Composition

| Component | Ingredient | Parts (by weight) |
|---|---|---|
| Isocyanate Component A | ISONATE ™ 2134L Polyisocyanate (Dow Chemical) | 58.91 |
| | Benzoyl Chloride (Stabilizer) | 0.05 |
| | Sub Total | 58.96 |
| Polyol Component B | NIAX ™ PPG 725 Polypropylene Oxide Polyol (Arco Chemical Co., Newton Square, PA) | 24.99 |
| | NIAX ™ PPG 425 Polypropylene Oxide Polyol (Arco Chemical Co., Newton Square, PA) | 9.90 |
| | DB-100 Antifoamer (Dow Chemical) | 0.18 |
| | Ionol Antioxidant (Shell Chemical Co.) | 0.48 |
| | Pluronic F-108 (BASF) | 3.99 |
| | 2,2'-Dimorpholinodiethyl Ether Catalyst (Huntsman Chemical, Austin, TX) | 1.50 |
| | Sub Total | 41.04 |
| | Total | 100.0 |

Sample casting tapes and splint materials were made by coating dry non-woven fabric backings containing PVP binder (Example 1; Runs 1A, 1C, 1D, and 1E) with the water-curable resin at a final resin to fabric coating weight of 75 %. After coating, each sample was further converted into approximately 3.35-m rolls wrapped around a 1.2-cm polyethylene core. The converting was done under minimal tension to avoid stretching the fabric. After winding, each roll was placed inside of an aluminum foil laminated pouch and heat sealed. All of the samples were allowed to age at least 14 hours prior to evaluating as cast or splint materials.

Evaluation as Cast Tapes

To evaluate as a cast tape, a sample of each resin-coated backing was removed from the aluminum pouch, dipped in 23° C. to 25° C. water, squeezed several times, removed from the water, and then squeezed a final time to remove any excess water. The tape was then immediately unrolled, wrapped around a subject's forearm, molded, and allowed to harden. During application, all of the casting tape samples exhibited good to exceptional conformability and moldability, and had the unique characteristic of being easily torn anywhere along their length. The torn portions of tape could then be applied to areas of the cast requiring maximum levels of strength. The resulting hardened casts were rigid and had good strength.

Evaluation as Splint Materials

To evaluate as a splint material, a resin-coated sample from the fabric backing of Example 1 (Run 1A) was removed from the aluminum pouch, unrolled, and cut into strips approximately 32.2 cm in length. Six strips were placed directly on top of each other to provide a six-layer, 7.6 cm×32.2 cm splint material. The six-layer splint was then dipped in water, immediately placed on a subject's forearm, and wrapped snugly against the forearm with an elastic type of compression wrap. The material hardened into a rigid form suitable for use as an orthopedic splint.

Other embodiments of the invention are within the scope of the following claims.

What is claimed is:

1. An orthopedic casting article comprising:
   a fibrous backing containing a water soluble binder; and
   a hardenable material associated with the fibrous backing, wherein the water soluble binder solubilizes upon wetting of the orthopedic casting article with water.

2. The article of claim 1, wherein the article is in the form of a casting tape.

3. The article of claim 1, wherein the article is in the form of a splint.

4. The article of claim 1, wherein the fibrous backing comprises a non-woven material.

5. The article of claim 1, wherein the fibrous backing comprises a carded non-woven web.

6. The article of claim 4, wherein the non-woven material comprises fibers selected from the group consisting of polyester, rayon, cotton, nylon, acrylic, polyethylene, polypropylene, fiberglass, polyacrylamide, carbon, and combinations thereof.

7. The article of claim 1, wherein the fibrous backing comprises a combination of crimped and straight fibers.

8. The article of claim 7, wherein the straight fibers are selected from the group consisting of high tenacity polyester cord, polyolefin fibers, ceramic fibers, and fiberglass.

9. The article of claim 1, wherein the fibrous backing comprises a compacted or microcreped fabric.

10. The article of claim 9, wherein the compacted or microcreped fibrous backing is selected from the group consisting of woven, non-woven, and knit fabrics.

11. The article of claim 1, wherein the fibrous backing further comprises a filler selected from the group consisting of carbon black, talc, calcium carbonate, silica, mica, hollow microspheres, solid microspheres, diatomaceous earth, and combinations thereof.

12. The article of claim 1, wherein the fibrous backing further comprises a fibrous filler selected from the group consisting of wallastonites, short fiber length chopped glass, short fiber length carbon fiber, fibrous pulps, synthetic pulps, metal fibers, whiskers, and combinations thereof.

13. The article of claim 1, wherein the water soluble binder is selected from the group consisting of polyvinylpyrrolidones, polyvinylpyrrolidone/vinyl acetate copolymers, polyvinyl alcohols, polyethylene oxides, polyacrylamides, polyacrylic acids, cellulose ether polymers, polyethyl oxazolines, esters of polyethylene oxide, esters of polyethylene oxide and polypropylene oxide copolymers, urethanes of polyethylene oxide, and urethanes of polyethylene oxide and polypropylene oxide copolymers.

14. The article of claim 1, wherein the water soluble binder comprises polyvinylpyrrolidone.

15. The article of claim 1, wherein the hardenable material comprises a water curable resin.

16. The article of claim 15, wherein the water curable resin comprises an isocyanate-functional prepolymer.

17. The article of claim 1, wherein the hardenable material is selected from the group consisting of liquid organometallic compounds, alkoxy silane functional polyurethane oligomers, silicates, and epoxy resins.

18. The article of claim 1, wherein the hardenable material comprises plaster of Paris.

19. The article of claim 1, wherein the article is tearable after wetting.

20. An article comprising:
    a non-woven fibrous backing containing a water soluble binder; and
    a water curable resin, wherein the water soluble binder solubilizes upon wetting of the article with water.

21. The article of claim 20, wherein the water soluble binder comprises polyvinylpyrrolidone.

22. A method of making an orthopedic casting article comprising applying a hardenable resin on a fibrous backing wherein the fibrous backing contains a water soluble binder, and wherein the water soluble binder solubilizes upon wetting of the orthopedic casting article with water.

23. A method of immobilizing a limb, comprising:
    providing an orthopedic casting article comprising a fibrous backing containing a water soluble binder, the fibrous backing having a hardenable material applied thereto;
    wetting the article with water to solubilize the water soluble binder; and
    applying the orthopedic casting article to the limb such that the limb is immobilized upon hardening of the hardenable material.

* * * * *